United States Patent
Viöl et al.

(10) Patent No.: US 10,743,727 B2
(45) Date of Patent: Aug. 18, 2020

(54) METHOD OF AND APPARATUS FOR DRYING AND PLASMA-ASSISTED DISINFECTION OF HANDS

(71) Applicant: Hochschule für angewandte Wissenschaft und Kunst Hildesheim/Holzminden/Goettingen, Hildesheim (DE)

(72) Inventors: Wolfgang Viöl, Adelebsen (DE); Stephan Wieneke, Goettingen (DE); Lars ten Bosch, Schellerten OT Ottbergen (DE); Robert Köhler, Goettingen (DE); Alexander Syring, Goettingen (DE)

(73) Assignee: HOCHSCHULE FÜR ANGEWANDTE WISSENSCHAFT UND KUNST HILDESHEIM/HOLZMINDEN/ GOETTINGEN, Hildesheim (DE)

( * ) Notice: Subject to any disclaimer, the term of this patent is extended or adjusted under 35 U.S.C. 154(b) by 92 days.

(21) Appl. No.: 15/976,176

(22) Filed: May 10, 2018

(65) Prior Publication Data

US 2018/0255984 A1 Sep. 13, 2018

Related U.S. Application Data

(63) Continuation of application No. PCT/EP2016/076251, filed on Oct. 31, 2016.

(30) Foreign Application Priority Data

Nov. 11, 2015 (DE) .................. 10 2015 119 446

(51) Int. Cl.
*A47K 10/48* (2006.01)
*A61L 2/14* (2006.01)
(Continued)

(52) U.S. Cl.
CPC ............ *A47K 10/48* (2013.01); *A61L 2/0011* (2013.01); *A61L 2/0094* (2013.01); *A61L 2/14* (2013.01);
(Continued)

(58) Field of Classification Search
CPC ..... A47K 10/48; A61L 2/0011; A61L 2/0094; A61L 2/14; A61L 2202/11;
(Continued)

(56) References Cited

U.S. PATENT DOCUMENTS

| | | |
|---|---|---|
| 8,607,472 B2 | 12/2013 | Ishii et al. |
| 2013/0202496 A1 | 8/2013 | Konesky |
| 2013/0283629 A1 | 10/2013 | Bueker |

FOREIGN PATENT DOCUMENTS

| | | |
|---|---|---|
| CN | 103 876 678 A | 6/2014 |
| EP | 2 223 704 A1 | 2/2010 |

(Continued)

OTHER PUBLICATIONS

International Preliminary Report on Patentability in co-pending, related PCT Application No. PCT/EP2016/076251, dated May 15, 2018.

*Primary Examiner* — Timothy C Cleveland
(74) *Attorney, Agent, or Firm* — Thomas | Horstemeyer, LLP

(57) ABSTRACT

To dry a hand with fingertips and a carpus, the palmar aspect and the dorsal aspect of the hand are blown dry, starting from the fingertips, by a pair of planar gas jets, wherein the gas jets of the pair run towards each other in the direction from the carpus to the fingertips at an angle of less than 180°. By applying high-voltage AC pulses with respect to ground to dielectrically shielded electrodes arranged next to both pla- (Continued)

nar gas jets, direct discharges are obtained across the hand on the palmar aspect thereof and on the dorsal aspect thereof.

18 Claims, 3 Drawing Sheets

(51) Int. Cl.
*H05H 1/24* (2006.01)
*A61L 2/00* (2006.01)
(52) U.S. Cl.
CPC ........ *H05H 1/2406* (2013.01); *A61L 2202/15* (2013.01); *H05H 2001/2412* (2013.01)
(58) Field of Classification Search
CPC .............. A61L 2202/15; H05H 1/2406; H05H 2001/2412; A61N 1/44
See application file for complete search history.

(56) References Cited

FOREIGN PATENT DOCUMENTS

| | | |
|---|---|---|
| EP | 2 277 424 A1 | 1/2011 |
| EP | 2 656 762 A2 | 4/2013 |
| JP | 2003-235757 | 8/2003 |
| JP | 1 796 281 B2 | 8/2005 |
| JP | 51-43223 | 11/2012 |
| JP | 2013-0244248 A | 12/2013 |
| JP | 57-46980 | 5/2015 |
| WO | 2007015043 A1 | 2/2007 |
| WO | 2014091191 A1 | 6/2014 |

METHOD OF AND APPARATUS FOR DRYING AND PLASMA-ASSISTED DISINFECTION OF HANDS

CROSS REFERENCE TO RELATED APPLICATIONS

This application is a continuation to International Application PCT/EP2016/076251 filed on Oct. 31, 2016, entitled "Method and Device for the Drying and Plasma-Assisted Disinfection of Hands" and claiming priority to German Patent Application DE 10 2015 119 446.5 filed on Nov. 11, 2015 and entitled "Verfahren und Vorrichtung zur Trocknung und plasmagestutzten Desinfektion von Händen".

FIELD

The present invention relates to a method of drying a hand having a palmar aspect, a dorsal aspect, a carpus and fingertips, wherein the palmar aspect and the dorsal aspect of the hand are blown off, starting at the fingertips, by a pair of planar gas jets, the gas jets of the pair running towards each other at an angle of less than 180°. Further, the invention relates to an apparatus for hand drying comprising a housing having a hand insertion opening and two slot nozzles arranged at the two longitudinal sides of the hand insertion opening and oriented at a slant angle into the housing to blow off a palmar aspect and a dorsal aspect of a hand inserted into the hand insertion opening by a pair of planar gas jets emerging from the slot nozzles.

BACKGROUND

A method of drying a hand and an apparatus for hand drying as outlined above are known from WO 2007/015043 A1. The known apparatus for hand drying comprises a hand insertion opening with two merged opening areas which are each provided for one hand and which are arranged side by side. A distance of the longitudinal sides of the hand insertion opening is 70 to 100 mm, i.e. about 85 mm, and this distance is reduced at both ends of the hand insertion opening and between its two opening areas to 50 to 80 mm, i.e. about 65 mm. At both longitudinal sides of the hand insertion opening, slot nozzles are arranged which are connected to a blower in the housing of the apparatus to blow planar gas jets out of the slot nozzles. The gas jets consist of air whose velocity is at least 80 m/s, preferably at last 100 or 150 m/s, more preferably about 180 m/s. Besides the hand insertion opening, the housing of the known apparatus has big lateral openings directly connected to the hand insertion opening, through which the blown out air of the gas jets passes into the surroundings of the apparatus. In this way, however, water blown away from the hands and germs blown away from the hands together with the water are delivered into the surroundings of the apparatus. The air which is sucked in by the blower for blowing it out of the slot nozzles is sucked in through a filter.

The angle between the planar gas jets emerging out of the slot nozzles by which the palmar aspect and the dorsal aspect of the respective hand are blown off is an obtuse angle, i.e. the slot nozzles are directed into the housing of the apparatus at a small slant angle only.

A further development of the apparatus for hand drying known from WO 2007/015043 A1 is disclosed in WO 2014/091191 A1. Here, the slot nozzles are oriented into the housing at a higher slant angle. The slant angle of the one slot nozzle is constant, whereas the slant angle of the opposing slot nozzle varies over the width of the hand insertion opening particularly in a range from 50° to 59° with regard to a horizontal plane of the hand insertion opening.

EP 2 223 704 A1 discloses a treatment apparatus for treating a body part of a patient with a non-thermal plasma. The apparatus is particularly intended for sterilizing a hand of a human. The apparatus has a housing for temporarily receiving the body part during the treatment and for applying a plasma to the body part within the housing. The housing has an insertion opening for inserting the body part into the housing. The housing further includes a plasma generator, a high voltage generator, an outer electrical insulation, a gas-permeable radiation shielding and a spacer. The plasma generator has two essentially planar arrangements for generating a dielectric barrier discharge. The one arrangement is arranged above, the other arrangement is arranged below a treatment area. Both arrangements have two electrodes and a dielectric barrier between the electrodes. By applying an alternating high voltage provided by the high voltage generator between the two electrodes, a dielectric barrier discharge is ignited which emits ultraviolet radiation.

JP 4 796 281 B2 discloses an apparatus for disinfection by means of a hot plasma jet. A dielectric barrier discharge is ignited in an air jet generated by a blower. The discharge also generates the desired heat of the hot plasma jet.

U.S. Pat. No. 8,607,472 B2 discloses an apparatus for hand drying in which an ion generator enriches air jets emerging out of slot nozzles with ions which have a sterilizing effect. In this known apparatus, water blown away from the hands is collected, and a part of the air blown out of the slot nozzles is once again sucked in by a blower connected to the slot nozzles and thus circulated. The ion generator generates the ions by means of a corona discharge between two electrodes which are arranged upstream of the slot nozzles.

EP 2 656 762 A2 (corresponding to US 2013/0283629 A1) discloses an apparatus for drying hands comprising a housing in which a cavity accessible from the outside is formed for receiving the hands to be dried by means of an airflow. Further, a blower for generating the airflow and means for reducing germs in the airflow are arranged in the housing. These means for reducing the germs may be a device for supplying a germ-reducing substance to the airflow, a plasma or ion source and/or a radiation source. The plasma or ion source may be a microwave or high frequency plasma or ion source. The radiation source may be a UV radiator or a dielectric barrier discharge lamp. The known apparatus may further have an air outlet conduit and an air inlet conduit communicating with the cavity in such a way that the airflow may be circulated through the air outlet conduit and the air inlet conduit as well as the cavity. The means for reducing the germs are particularly arranged in the area of the air outlet conduit. They may, however, also be arranged in the cavity, if they are radiation sources, for example.

CN 103 876 678 A discloses an apparatus for hand drying comprising a blower, a heating wire, an electrode plate and an alternating voltage source. The blower generates a warm airflow onto the electrode plate by means of the heating wire. When a wet washed hand is stretched out on the electrode plate, discharges occur with regard to the wet surface of the hand. These discharges kill germs on the surface of the hand and remove water. Together with the warm airflow, the hand is dried quickly. The alternating voltage source provides an alternating voltage between the electrode plate and a grid, an isolator plate being arranged in between. The grid is facing the and the blower arranged upstream of the heating wire. It is not disclosed how in this arrangement a discharge for generating a plasma may be generated by means of the alternating voltage source with regard to the wet hand which has to be arranged on the grid to be subjected to the warm airflow.

JP 2013-244248 A discloses an apparatus for hand drying having a housing with a hand insertion opening. The hand insertion opening leads between nozzle plates with a plurality of nozzles which are oriented into the housing at a slant angle to blow off the hand inserted into the housing. On the backsides of the nozzle plates facing away from the hand, pairs of electrode plates are provided which have through-openings corresponding to the nozzles in the nozzle plates. At its opposing surfaces, the two electrode plates of each pair are provided with a dielectric coating. By applying an alternating voltage between the two electrodes, a plasma is ignited in air which is supplied by a blower before the air is blown out through the nozzle plates onto the hand.

There still is a need of a method of drying a hand and an apparatus for hand drying which efficiently kill germs on the surface of the hand and which efficiently avoid that germs from the hand are distributed into the surroundings.

SUMMARY OF THE INVENTION

The invention relates to a method of drying a hand, the hand having a palmar aspect, a dorsal aspect, a carpus and fingertips. The method comprises blowing off the palmar aspect and the dorsal aspect beginning at the fingertips of the hand with a pair of planar gas jets, the gas jets of the pair running towards each other in a direction from the carpus to the fingertips at an angle of less than 180°, and generating direct discharges on the palmar aspect and the dorsal aspect of the hand by applying high frequent alternating high voltage pulses with regard to ground to dielectrically shielded electrodes arranged next to both planar gas jets.

The invention further relates to an apparatus for hand drying. The apparatus comprises a housing having a hand insertion opening, the hand insertion opening having two longitudinal sides and two slot nozzles, each of the two slot nozzles being arranged on one of the longitudinal sides of the hand insertion opening, the two slot nozzles being oriented into the housing at a slant angle to blow off a planar aspect and a dorsal aspect of a hand inserted into the hand insertion opening with a pair of planar gas jets emerging out of the slot nozzles. The apparatus further comprises dielectrically shielded electrodes arranged next to the slot nozzles, and an alternating high voltage source connected to the dielectrically shielded electrodes and configured to apply high frequency alternating high voltage pulses with regard to ground to the dielectrically shielded electrodes, the alternating high voltage pulses generating direct discharges on the palmar aspect and the dorsal aspect of the hand inserted into the hand insertion opening.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

FIG. 2 illustrates the design of a slot nozzle with adjacent dielectrically shielded electrodes in the apparatus according to FIG. 1; and.

DETAILED DESCRIPTION

Figure 1:
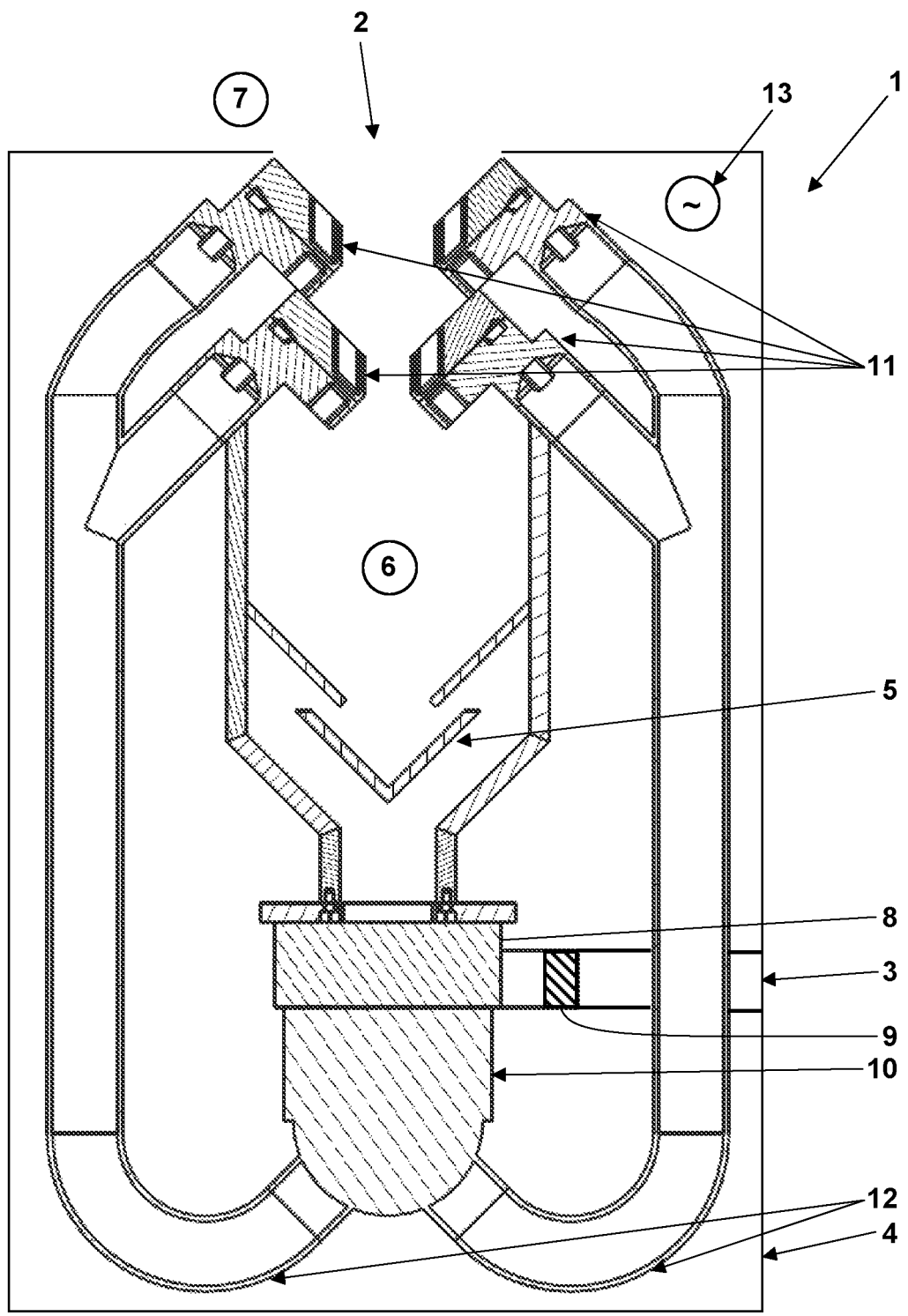
FIG. 1 is a section through an apparatus for hand drying according to the present invention.

In the method according to the invention of drying a hand having a carpus and fingertips, the palmar aspect and the dorsal aspect of the hand are blown off with a pair of planar gas jets starting at the fingertips. The gas jets of the pair run towards each other in the direction from the carpus to the fingertips at an angle of less than 180°, preferably at an angle between 60° and 150°. Further, direct discharges are generated on the palmar aspect and the dorsal aspect of the hand by applying alternating high voltage pulses with regard to ground to dielectrically shielded electrodes arranged adjacent to both planar gas jets.

By means of the gas jets which due to running towards each other strike the respective palmar or dorsal aspect of the hand at a slant angle most of the water adhering to the hand is blown away from the hand to be dried. In the method according to the invention, however, it is not intended to completely dry the hand to be dried at once. Instead, it is even desired that the hand remains moist initially. This makes it considerably easier to ignite direct discharges above the hand by applying the alternating high voltage pulses with regard to ground to the dielectrically shielded electrodes arranged adjacent to the two planar gas jets. Further, these direct discharges cause a chemical change or activation of the moisture film still present on the hand, which imparts a strong germ-killing property to the moisture film. Before the germs which are present on the surface of the hand are released from the hand by also drying this moisture film, they are killed in the method according to the invention.

In the direct discharges above the hand generated according to the invention, the hand is effective as a capacitive counter electrode to the respective dielectrically shielded electrode to which the alternating high voltage pulses are applied with regard to ground. This means, there is no gas discharge between the dielectrically shielded electrodes to which the alternating high voltage pulses are applied synchronously but between each of these dielectrically shielded electrodes and the hand. The direct discharges above the hand are dielectric barrier discharges due to the dielectric shielding of the electrodes, i.e. the electrical currents flowing are only small. Further, the electrical currents flowing due to these direct discharges, with increasing frequency of the high frequency alternating high voltage pulses, which is at least some kilohertz, preferably 10 kHz up to several 10 kHz, i.e. 200 kHz at maximum, and, for example, about 30 kHz, only flow at the surface and not in the volume of the hand because of the so called skin effect. The electrical currents flowing at the surface of the hand also have a killing effect on the germs which are present here. At the same time, it is ensured that the currents do not get into the tissue and cause irrigations or even damages there. In the method according to the invention, even at the surface of the hand, no significant increases in temperature of the hand or its skin take place as a direct result of the direct discharges above the hand or as a result of the electrical currents flowing at the surface of the skin. Such increases in temperature are not only avoided due to the limitation to the electrical currents by the dielectric barrier to the direct discharges provided by the dielectric shielding of the electrodes, but also by the gas jets directed onto the hand and their cooling effect.

If a frequency of the alternating high voltage pulses is mentioned here, the numbers indicated relate to the frequency of the pulse sequence at which pairs of a negative and a positive voltage pulse follow to each other. The individual alternative high voltage pulses, the individual pulse pairs or groups of alternative high voltage pulses may be arranged at comparatively long intervals with regard to each other so that their voltage alteration rates may correspond to those of voltage pulses directly following to each other and having a much higher frequency. For example, the pulses of each pulse pair may be arranged at a considerably shorter interval of time than half the reciprocal value of the pulse pair (follow up) frequency. This makes it easier to ignite the direct dielectric barrier discharges above the hand at alternating voltages of limited amplitude of typically few kV to few 10 kV, particularly at alternating voltages in a range from 5 kV to 30 kV.

The gas jets by which the hand, in the method according to the invention, is at first blown off to blow away any water except of a purposefully left moisture film may particularly be air jets. In that the gas jets are not provided for directly removing any moisture from the hand, a blower for generating the air jets may be of a comparatively small dimension, and the noise development associated with the generation and blowing out of the gas jets is also limited. The direct discharges generated above the hand are not associated with any relevant noise.

In the method according to the invention, the dielectrically shielded electrodes may be held at a distance across the hand which increases in direction from the fingertips towards the carpus. Generally, the distance of the electrodes which are facing each other across the hand may be varied for this purpose. It is, however, easier that the distance of the electrodes increases in the direction from the fingertips to the carpus in that the electrodes are arranged in a V-configuration or in that several pairs of electrodes with different distances across the hand are provided. Particularly, the direct discharges may be generated with at least two pairs of dielectrically shielded electrodes which are arranged one behind the other in the direction from the fingertips to the carpus and which are extended transverse to the direction from the fingertips to the carpus.

The gas jets may particularly be generated at a velocity of its gas with regard to the surroundings of 100 to 350 km/h. This means, they are rather quick gas jets. The gas jets are, however, not so fast as it would be necessary for immediately drying the hand completely. For the purpose of immediately drying the hand completely, WO 2007/015043 A1 indicates velocities of preferably at least 100 or 150 m/s, more preferably of about 180 m/s, 100 m/s being exactly 360 km/h and 180 m/s being nearly 650 km/h.

In the method according to the invention, the palmar aspect and the dorsal aspect of the hand are preferably blown off beginning at the fingertips with at least two pairs of planar gas jets arranged one behind the other in the direction from the fingertips to the carpus. The gas jets of each pair run towards each other in the direction from the carpus to the fingertips at an angle of less than 180°. Thus, particularly the fingers of the hand at its palmar aspect and its dorsal aspect are blown off with two gas jets one after the other so that water forming more than a moisture film is reliably removed even out of the spaces between the fingers.

Particularly, the gas jets may be formed by blowing gas out of slot nozzles which run along the dielectrically shielded electrodes which are extended transverse to the direction from the fingertips to the carpus. In the gas, out of which at least one of the gas jets is formed, an additional dielectric barrier discharge may be generated. This additional dielectric barrier discharge enriches the gas, which is then blown as a gas jet onto the hand, by reactive species which have an additional germ-killing effect. Further, the dielectric barrier discharge in the gas serves for sterilization of the gas as such.

Preferably, the dielectric barrier discharge in the gas out of which the at least one gas jet is formed is generated between a dielectrically shielded electrode running along the respective slot nozzle and a dielectrically shielded counter electrode running in parallel thereto on the other side of the slot nozzle. This dielectrically shielded counter electrode is preferably held on earth or ground potential. In contrary to the dielectrically shielded electrode running along the respective slot nozzle at which the alternating high voltage with regard to ground is present, the dielectrically shielded counter electrode is no end point of any direct discharge generated above the hand.

In the method according to the invention, the water blown away from the hand is preferably collected and accumulated or removed, wherein germs included in the water may be killed in any known and suitable way. In any case, it is avoided that the germs included in the water are getting into the surroundings by atomizing or evaporating the water.

Due to the gas jets running towards each other at an angle of less than 180°, air out of the surroundings is entrained. Thus, a gas flow or stream resulting from blowing off with the gas jets may only be circulated in part for forming the gas jets because its volume is increased by the entrained air. Instead, this increase to the gas flow has to be removed continuously. In the method according to the invention, this is preferably implemented by blowing off gas through a suitable filter which holds back and preferably also kills germs included in the blown off part of the airflow. Preferably, ozone which is generated by the direct discharge above the hand and any additional dielectric barrier discharge in the gas is also reduced in the filter. On the other hand, reducing the ozone in the circulated gas flow is not necessary or even suitable, because it may be used on for killing germs.

An apparatus for hand drying comprising a housing with a hand insertion opening and two slot nozzles arranged at both longitudinal sides of the hand insertion opening, which are oriented into the housing at a slant angle, to blow off the palmar aspect and the dorsal aspect of a hand inserted into the hand insertion opening with a pair of planar gas jets emerging out of the slot nozzles is characterized according to the invention in that dielectrically shielded electrodes are arranged next to both slot nozzles and that an alternating high voltage source is connected to the dielectrically shielded electrodes to apply alternating high voltage pulses with regard to ground to the dielectrically shielded electrodes, wherein the alternating high voltage pulses generate direct discharges above the palmar aspect and the dorsal aspect of the hand inserted into the hand insertion opening.

A hand inserted through the hand insertion opening into the housing of the apparatus according to the invention is both blown off with the planar gas jets and treated by the direct discharges and by reactive species which are generated as a result of the discharges in such a way that germs at the surface, i.e. on the skin of the hand, are killed. Here, due to blowing the water off the hand without completely drying the hand at once, particularly good preconditions for igniting the direct discharges and for providing reactive species and other germ-killing conditions at the surface of the hand are provided.

The dielectrically shielded electrodes of the apparatus according to the invention are held at a distance across the hand insertion opening which gets smaller in the direction into the housing. The electrodes may be elongated into the housing and arranged in a V-configuration, or several electrode pairs are arranged across the hand insertion opening one after the other in the direction into the housing. All these electrodes are connected to the alternating high voltage source. Generally, all electrodes may be connected to a same output of the alternating high voltage source. For direct discharges between the hand and all electrodes, it is, however, preferred if the alternating high voltage source has separate outputs or even separate partial sources for the individual electrodes or individual pairs of electrodes.

The distance between the dielectrically shielded electrodes of the first pair in the direction into the housing may be 5 to 8 cm, whereas the distance of the dielectrically shielded electrodes of the second pair in the direction into the housing may be 2 to 5 cm. The first distance is adjusted to the thickness of a typical hand in the area of its carpus; the second distance is adjusted to the thickness of a typical hand in the area of its fingers.

The apparatus according to the invention, preferably also has at least two pairs of slot nozzles oriented towards each other at a slant angle and running transverse to the direction into the housing. Particularly, one slot nozzle may run along each dielectrically shielded electrode.

A dielectrically shielded counter electrode on ground potential may be arranged opposite to at least one of the dielectrically shielded electrodes across its neighboring slot nozzle in such a way that the alternating high voltage pulse applied to the dielectrically shielded electrode additionally ignite or generate a dielectric barrier discharge in the slot nozzle. In this way, the planar gas jet emerging out of the slot nozzle already includes reactive species which are generated by the dielectric barrier discharge in the slot nozzle. Further, germs in the gas of the gas jet are killed by the dielectric barrier discharge in the slot nozzle.

Preferably, the apparatus according to the invention comprises, within the housing, a collection gutter for water blown away from the hand, the collection gutter, in the direction into the housing, being arranged behind the slot nozzles. By means of this collection gutter, the water is collected and removed. In this way it is avoided that the water is atomized or evaporated and gets into the surroundings of the apparatus together with any germs included.

A gas guidance in the housing of the apparatus according to the invention may have a recirculation channel guiding back to the slot nozzles with a blower arranged therein, and an blow-off channel leading into the surroundings of the housing with a filter arranged therein. The gas jets entrain air out of the surroundings into the housing and thus continuously increase the moved gas volume. Correspondingly, it is not possible to recirculate the entire gas flow or air stream. Instead, a part of the air stream has always to be removed or blown off into the surroundings. The blow-off channel serves for this purpose. The filter arranged in the blow-off channel may particularly hold back germs and reduce ozone which is generated by the gas discharges in the apparatus. In the recirculation channel, however, a part of the air is circulated within the apparatus according to the invention, and in this way the air movement in the surroundings of the apparatus is minimized.

Now referring in greater detail to the drawings, the apparatus 1 according to the present invention depicted in FIG. 1 comprises a housing 4 which is closed except of a hand insertion opening 2 and an blow-off channel 3 which opens into the surroundings 7 of the apparatus 1. Through the hand insertion opening, hands to be dried can be inserted between plasma nozzles 11. The plasma nozzles 11 are arranged in pairs across the hand insertion opening 2, a distance of the plasma nozzles 11 of a first or back pair in direction into the housing 4 being longer than a distance of a second or front pair in this direction. By means of the plasma nozzles 11, the hands inserted into the hand insertion opening 2 are simultaneously blown off with planar gas jets and treated with plasma as it will be described in more detail later. The water blown away from the hands is collected in a collection gutter 5 at the ground of a collection room 6 into which the hands enter with their fingertips and which particularly receives the gas of the gas jets and the water blown away from the hands with these gas jets. Via the collection gutter 5, the water is forwarded to a collection container not depicted here or to a drainage. A disinfection means or filter for holding back or killing germs may be arranged in the collection container or the drainage or in a conduit leading thereto. The total gas of the gas jets and of air entrained by the gas jets out of the surroundings 7 into the housing 4 gets into a filter 8 for removing germs within the apparatus 1 according to FIG. 1. This filter 8, however, is only an option. On the other hand, a filter 9 in the blow-off channel 3 has the be provided for not only filter germs but also ozone off the air blown-off into the surroundings 7. That part of the air stream which is not blown off via the blow-off channel 3 into the surroundings 7 is recycled by a blower 10 via recirculation channels 12 to the plasma nozzles 11. Besides the recirculation channels 12, the plasma nozzles 11, via electrical connection lines not depicted here, are connected to an alternating high voltage source 13 of the apparatus 1. If, in the operation of the apparatus 1, there is no overpressure in the collection room 6 as compared to the surroundings 7, the blow-off channel 3 has to be provided with an additional blower, or the blow-off channel 3 has to branch off downstream of the blower 10 to be able to remove excess air out of the apparatus 1 into the surroundings 7.

Figure 2:
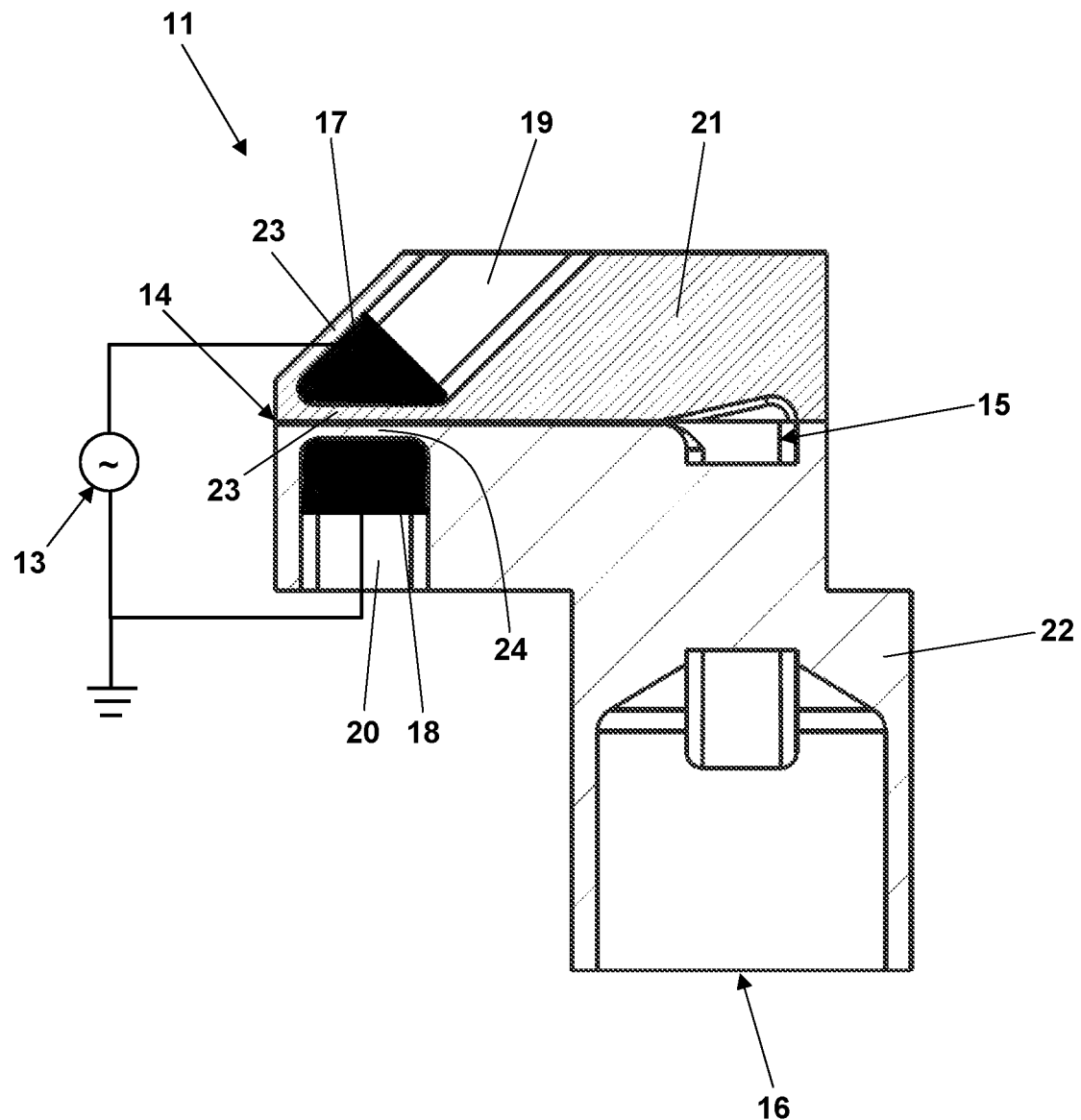

FIG. 2 shows one of the plasma nozzles 11 according to FIG. 1 in a separate enlarged view. The plasma nozzle 11 includes a slot nozzle 14 out of which one of the planar gas jets emerges. The slot nozzle 14 is connected to a gas inlet 16 of the plasma nozzle 11 via a prechamber 15. The slot size of the slot nozzle 14 is about 0.3 mm here. The length of the slot nozzle orthogonal to the drawing plane is about 260 mm here, so that two hands arranged side by side in this direction may be blown off and plasma-treated simultaneously. Directly in front of the opening of the slot nozzle 14 into the surroundings 7 two electrodes 17 and 18 are facing each other across the slot nozzle 14. The electrodes 17 and 18 are arranged in pockets 19 and 20 of two components 21 and 22 of the plasma nozzle 11 which are mechanically connected to each other. These components 21 and 22 are made of a dielectric material. The components 21 and 22 thus form dielectric shieldings 23 and 24 of the electrodes 17 and 18.

By means of the alternating high voltage source 13, high frequent alternating high voltage pulses are applied between the electrodes 17 and 18, the electrode 18 being grounded. These alternating high voltage pulses generate a dielectric barrier discharge between the dielectric shieldings 23 and 24 of the electrodes 17 and 18 within the slot nozzle 14. As a result of this dielectric barrier discharge, a cold plasma is formed in the gas supplied to the slot nozzle 14 so that the gas jet emerging out of the slot nozzle 14 includes reactive species which are able to kill germs. These reactive species also kill germs included in the gas supplied to the slot nozzle 14. Further, the dielectric shielding 23 of the electrode 17 to which the alternating high voltage pulses of the alternating high voltage source 13 are applied with regard to earth or ground is formed such that direct discharges above the hand which is brought next to it are additionally generated. The thicknesses of the dielectric shieldings 23 and 24, the working distance of the dielectric shieldings 23 and 24 across the slot nozzle 14 and the alternating high voltage pulses of the alternating high voltage source 13 are adjusted with regard to each other in such a way that the direct discharges above the hand and the dielectric barrier discharge in the slot nozzle 14 are generated simultaneously. In the formation of the components 21 and 22 from, for example, PMMA, the thickness of the dielectric shielding 23 may, for example, be 2 mm, and the thickness of the dielectric shielding 24 may, for example, be 1.7 mm. To homogenously generate the dielectric barrier discharge within the slot nozzle 14 over the entire length of the slot nozzle 14, the electrodes 17 and 18 inclusive of their dielectric shieldings 23 and 24 are to be arranged with regard to each other exactly parallel. Further, it is an advantage for the homogeneity of the dielectric barrier discharge and the direct discharges above the hand if at least the electrode 17 has a rough surface. This rough surface may, for example, be realized by making the electrodes 17 and 18 of a powder starting material. This starting material, for example brass powder, may be casted with silicone which wets the starting material completely and without leaving entrapped air and which electrically insulates the electrodes 17 and 18 by filling the pockets 19 and 20 and their back sides. Further, a separate partial source of the alternating high voltage source 13 may be provided for each plasma nozzle so that current flowing due to discharges in the area of one plasma nozzle 11 have no influence on the function of the other plasma nozzle 11.

Figure 3:
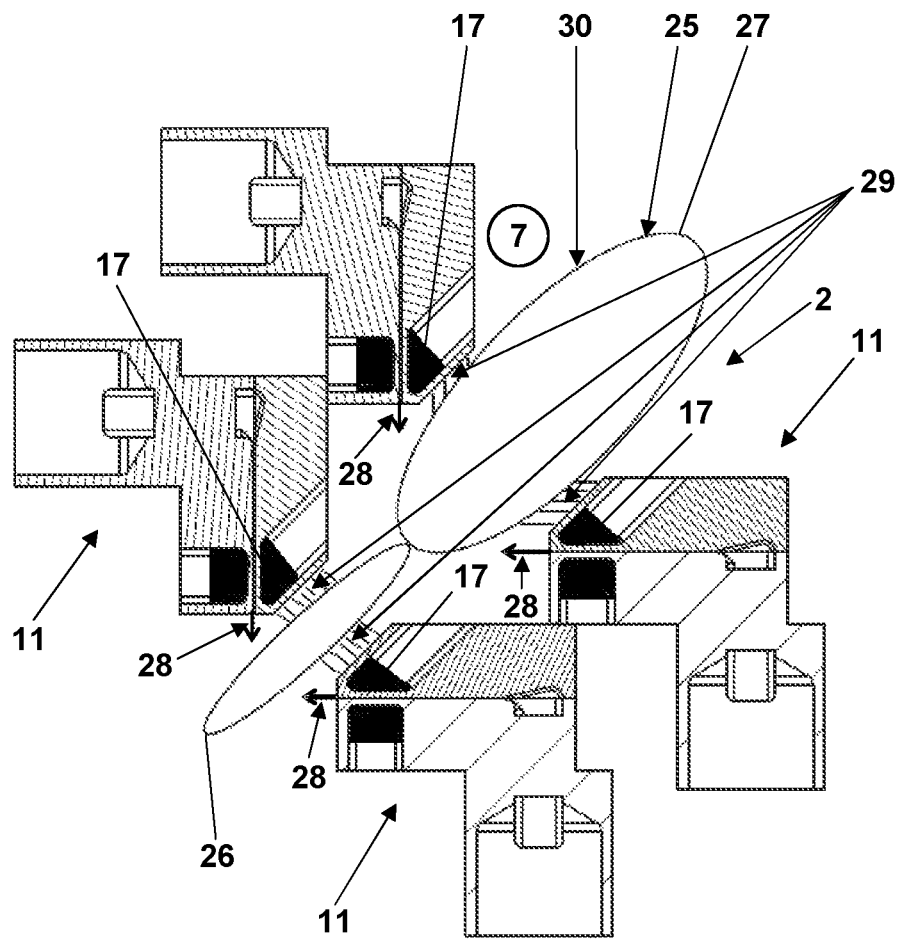
FIG. 3 illustrates the function of the apparatus of FIG. 1 according to the present invention.

FIG. 3 schematically depicts a hand 25 extending from fingertips 26 to a carpus 27 and inserted between the four plasma nozzles 11 according to FIG. 1. The palmar aspect and the dorsal aspect of the hand 25 are blown off with the planar gas jets 28 emerging out of the plasma nozzles 11. These gas jets already include reactive species which are suitable for killing germs due to the dielectric barrier discharges in the plasma nozzles 11. Further, direct discharges 29 are generated above the hand 25 in the area of the electrodes to which the alternating high voltage pulses are applied with regard to ground. The direct discharges 29 are assisted by a moisture film still existing on the surface 30, i.e. on the skin of the hand 25. Further, the direct discharges 29 modify the composition of this moisture film so that a strong germ-killing effect results. Particularly, the moisture film will be acidified by the direct discharges 29, and it may have an increased peroxide and nitrite concentration, both resulting in a germ-killing effect. The planar gas jets 23 are arranged in pairs at an angle which is essentially a right angle here. The dielectric shielding of the electrodes to which the alternating high voltage pulses are applied with regard to ground and from which the direct discharges 29 start are arranged in pairs parallel with regard to each other and with regard to the surface 30 of the hand. The air velocity in the gas jets 28 may be nearly 350 km/h. The output voltage of the alternating high voltage source may be about 20 kV. The repetition frequency of the alternating high voltage pulses may be about 30 kHz.

Many variations and modifications may be made to the preferred embodiments of the invention without departing substantially from the spirit and principles of the invention. All such modifications and variations are intended to be included herein within the scope of the present invention, as defined by the following claims.

We claim:

1. An apparatus for hand drying, the apparatus comprising
   a housing having a hand insertion opening, the hand insertion opening having two longitudinal sides,
   two slot nozzles, each of the two slot nozzles being arranged on one of the longitudinal sides of the hand insertion opening, the two slot nozzles being oriented into the housing at a slant angle to blow off a palmer aspect and a dorsal aspect of a hand inserted into the hand insertion opening with a pair of planar gas jets emerging out of the slot nozzles,
   dielectrically shielded electrodes arranged next to the slot nozzles, and
   an alternating high voltage source connected to the dielectrically shielded electrodes and configured to apply high frequency alternating high voltage pulses with regard to ground to the dielectrically shielded electrodes, the dielectrically shielded electrodes being arranged such that the alternating high voltage pulses applied to the dielectrically shielded electrodes generate direct discharges on the palmar aspect and the dorsal aspect of the hand inserted into the hand insertion opening.

2. The apparatus of claim 1, wherein the dielectrically shielded electrodes are held at a distance across the hand insertion opening, the distance decreasing in a direction into the housing.

3. The apparatus of claim 1, wherein, in a direction into the housing, two pairs of dielectrically shielded electrodes which are extended transverse to the direction into the housing and which are connected to the alternating high voltage source are arranged one after the other, and wherein a distance between the two dielectrically shielded electrodes of a front pair of the two pairs is smaller than a distance between the two dielectrically shielded electrodes of a back pair of the two pairs.

4. The apparatus of claim 3, wherein the distance of the dielectrically shielded electrodes of the front pair of the two pairs is 2 cm to 5 cm, and wherein the distance of the dielectrically shielded electrodes of the back pair is 5 cm to 8 cm.

5. The apparatus of claim 1, wherein, in a direction into the housing, a further pair of slot nozzles which are directed into the housing at a slant angle is arranged behind the pair of slot nozzles.

6. The apparatus of claim 1, wherein, in a direction into the housing, behind the slot nozzles a collection gutter for water blown away from the hand is arranged in the housing.

7. The apparatus of claim 1, wherein a gas guidance within the housing has a recirculation channel guiding back to the slot nozzles, a blower arranged in the recirculation channel, an blow-off channel guiding into the surroundings and a filter arranged in the blow-off channel.

8. The apparatus of claim 1, wherein the alternating high voltage source has a separate partial source for each of the dielectrically shielded electrodes for separately applying the alternating high voltage pulses to the respective dielectrically shielded electrode.

9. The apparatus of claim 1, wherein a blower is connected to the two slot nozzles, wherein the blower is configured for providing the pair of planar gas jets at a gas velocity of 100 to 350 km/h with regard to the surroundings of the apparatus.

10. An apparatus for hand drying, the apparatus comprising
- a housing having a hand insertion opening, the hand insertion opening having two longitudinal sides,
- two slot nozzles, each of the two slot nozzles being arranged on one of the longitudinal sides of the hand insertion opening, the two slot nozzles being oriented into the housing at a slant angle to blow off a palmar aspect and a dorsal aspect of a hand inserted into the hand insertion opening with a pair of planar gas jets emerging out of the slot nozzles,
- dielectrically shielded electrodes arranged next to the slot nozzles, and
- an alternating high voltage source connected to the dielectrically shielded electrodes and configured to apply high frequency alternating high voltage pulses with regard to ground to the dielectrically shielded electrodes, the dielectrically shielded electrodes being arranged such that the alternating high voltage pulses applied to the dielectrically shielded electrodes generate direct discharges on the palmar aspect and the dorsal aspect of the hand inserted into the hand insertion opening,
- wherein at least one of the dielectrically shielded electrodes is facing a dielectrically shielded counter electrode held on ground potential across a neighboring one of the slot nozzles such that the alternating high voltage pulses applied to the dielectrically shielded electrode cause a dielectric barrier discharge in the neighboring one of the slot nozzles.

11. The apparatus of claim 10, wherein the dielectrically shielded electrodes are held at a distance across the hand insertion opening, the distance decreasing in a direction into the housing.

12. The apparatus of claim 10, wherein, in a direction into the housing, two pairs of dielectrically shielded electrodes which are extended transverse to the direction into the housing and which are connected to the alternating high voltage source are arranged one after the other, and wherein a distance between the two dielectrically shielded electrodes of a front pair of the two pairs is smaller than a distance between the two dielectrically shielded electrodes of a back pair of the two pairs.

13. The apparatus of claim 12, wherein the distance of the dielectrically shielded electrodes of the front pair of the two pairs is 2 cm to 5 cm, and wherein the distance of the dielectrically shielded electrodes of the back pair is 5 cm to 8 cm.

14. The apparatus of claim 10, wherein, in a direction into the housing, a further pair of slot nozzles which are directed into the housing at a slant angle is arranged behind the pair of slot nozzles.

15. The apparatus of claim 10, wherein, in a direction into the housing, behind the slot nozzles a collection gutter for water blown away from the hand is arranged in the housing.

16. The apparatus of claim 10, wherein a gas guidance within the housing has a recirculation channel guiding back to the slot nozzles, a blower arranged in the recirculation channel, an blow-off channel guiding into the surroundings and a filter arranged in the blow-off channel.

17. The apparatus of claim 10, wherein the alternating high voltage source has a separate partial source for each of the dielectrically shielded electrodes for separately applying the alternating high voltage pulses to the respective dielectrically shielded electrode.

18. The apparatus of claim 10, wherein a blower is connected to the two slot nozzles, wherein the blower is configured for providing the pair of planar gas jets at a gas velocity of 100 to 350 km/h with regards to the surroundings of the apparatus.

* * * * *